United States Patent
Adair et al.

(10) Patent No.: US 12,339,909 B2
(45) Date of Patent: Jun. 24, 2025

(54) HIERARCHICAL TAGGING FOR PERSONALIZED MATCHING

(71) Applicant: Vitalxchange, Inc., North Royalton, OH (US)

(72) Inventors: Jeffrey B. Adair, Cuyahoga Falls, OH (US); Charulatha Ramanathan, Solon, OH (US); Ketal C. Patel, Cleveland, OH (US); Jiyan Gardi, Laguna Hills, CA (US)

(73) Assignee: VITALXCHANGE, INC., North Royalton, OH (US)

( * ) Notice: Subject to any disclaimer, the term of this patent is extended or adjusted under 35 U.S.C. 154(b) by 7 days.

(21) Appl. No.: 18/462,247

(22) Filed: Sep. 6, 2023

(65) Prior Publication Data
US 2024/0078266 A1    Mar. 7, 2024

Related U.S. Application Data

(60) Provisional application No. 63/404,041, filed on Sep. 6, 2022.

(51) Int. Cl.
*G06F 16/9035* (2019.01)
*G06F 16/9038* (2019.01)

(52) U.S. Cl.
CPC ...... *G06F 16/9035* (2019.01); *G06F 16/9038* (2019.01)

(58) Field of Classification Search
None
See application file for complete search history.

(56) References Cited

U.S. PATENT DOCUMENTS

| 7,606,810 B1 * | 10/2009 | Jeavons | G06Q 30/02 707/999.005 |
| 8,548,828 B1 | 10/2013 | Longmire | |
| 2006/0224552 A1 * | 10/2006 | Riezler | G06F 16/337 |

(Continued)

*Primary Examiner* — Kannan Shanmugasundaram
(74) *Attorney, Agent, or Firm* — Tarolli, Sundheim, Covell & Tummino LLP

(57) ABSTRACT

As an example, a system includes a hierarchical tag database that includes a plurality of tags arranged according to a hierarchical data schema for a number of tag hierarchies, and tags within each level of a respective tag hierarchy have a different specificity relative to each other level of the respective tag hierarchy. The data can also include profile tag data for a given user. The system can also include a processor configured to access the media and execute the instructions to expand each of the stored profile tags for the given user to provide an expanded profile tag data set for the given user, in which the expanded profile tag data set includes each of the assigned profile tags and each one or more higher-level tag in each associated tag hierarchy to which each of the assigned profile tags belongs. The instructions can also be programmed to determine which tags in the expanded profile tag data set match corresponding item tags representative of available actions, services, products and/or activities. The instructions can also be programmed to generate a results list representative of a matching set of the actions, services, products and/or activities based on the determination. At least a portion of the results list can be presented in a user-perceptible format.

20 Claims, 11 Drawing Sheets

(56) References Cited

U.S. PATENT DOCUMENTS

| | | | |
|---|---|---|---|
| 2008/0162731 A1* | 7/2008 | Kauppinen | G06Q 30/02 |
| | | | 709/250 |
| 2014/0136373 A1 | 5/2014 | Kinsey, II et al. | |
| 2017/0193171 A1 | 7/2017 | Perlroth et al. | |
| 2020/0168335 A1 | 5/2020 | Lassoued et al. | |
| 2021/0020275 A1 | 1/2021 | Krishnan et al. | |
| 2024/0028654 A1* | 1/2024 | Serbinis | G06F 16/3347 |

* cited by examiner

HIERARCHICAL TAGGING FOR PERSONALIZED MATCHING

RELATED APPLICATION

This application claims priority to U.S. Provisional Patent Application No. 63/404,041, filed on Sep. 6, 2022, which is incorporated herein by reference in its entirety.

TECHNICAL FIELD

This description relates to using hierarchical tagging to perform personalized matching to health-related actions, products, and/or services.

BACKGROUND

Both medical training as well as innovations in healthcare have focused on highly specialized treatment strategies at organ level or sub-organ level. Modern medicine has become more about prescribing treatments rather than educate and empower patients to lead healthier lives or find problems early.

While it is widely recognized that patient advocacy, engagement, and clinical literacy could have a huge impact to clinical outcomes, there are several barriers:
1. Healthcare information is overwhelming to most patients because it is predominantly presented using medical jargon, legal appropriate terminology that too, from a clinical provider standpoint.
2. Healthcare information is very general and not personalized to the situation of the patient and their family.
3. While patients can get personalized advice from their doctors, the access is infrequent because it is reliant on the busy schedule of a doctor and behind an inconvenient appointment system.
4. The human body is a complex system with multiple physical and psychological triggers and substrates for illness or disease. Today's hyper-specialized medical environment focuses on one particular organ system at time rather than holistically focus on the patient.

These barriers have resulted in patients feeling overwhelmed, unable to take charge of their own health, and 'googling' for health data that suits their particular situation.

SUMMARY

One example relates to one or more non-transitory computer readable medium having instructions executable by one or more processors. The instructions can include code programmed to store a hierarchical tag database that includes a plurality of tags arranged according to a hierarchical data schema for a number of tag hierarchies. Each tag hierarchy has one or more levels, and each level in a respective tag hierarchy includes one or more tags. Tags within each level of a respective tag hierarchy have a different specificity relative to each other level of the respective tag hierarchy. The instructions can also include code programmed to store profile tags for a given user, in which the stored profile tags for the given user include one or more tags that have been assigned to the given user at a respective level in an associated tag hierarchy defined by the hierarchical data schema. The instructions can also include code programmed to perform matching between the profile tags and item tags representative of actions, services, products and/or activities. The instructions to match can further include instructions to expand each of the stored profile tags for the given user to provide an expanded profile tag data set for the given user, in which the expanded profile tag data set includes each of the assigned profile tags and each one or more higher-level tag in each associated tag hierarchy to which each of the assigned profile tags belongs. The instructions to match can further include instructions to determine which tags in the expanded profile tag data set match corresponding item tags representative of available actions, services, products and/or activities. The instructions to match can further include instructions to generate a results list representative of a matching set of the actions, services, products and/or activities based on the determination.

In an example, the instructions to expand are invoked in response to or as part of executing the instructions to perform the matching.

In another example, the instructions further include instructions to compute a score for each of the matches determined between the item tags and the tags in the expanded profile tag data set, in which the score for each of the matches depends on the level of hierarchy for each of matching tags, and the set of the actions, services, products and/or activities arranged in the results list is based on the respective scores. The instructions can also be programmed to compute the score is based on at least two of:
 a number of matching tags;
 a weighting applied to each of the matching tags according to weighting schedule;
 a penalty applied to reduce a value of the respective scores based on an absolute and/or relative quantity of matching tags.

In another example, each of the stored profile tags for the given user includes a tag within a single most-specific level of each associated tag hierarchy that has been assigned for the given user. The instructions to expand the assigned profile tags for the given user can be further programmed to:
 search a tag database containing a complete hierarchical description for tags within each tag hierarchy defined by the hierarchical data schema;
 identify each higher-level tag to which each of the stored profile tags belongs in each tag hierarchy; and
 generate the expanded profile tag data set for the given user to include each of the stored profile tags and the identified higher-level tags in each of the tag hierarchies.

In another example, the instructions are further programmed to get item tags assigned to each of the available actions, services, products and/or activities, and the instructions to determine which of the tags in the expanded profile tag data set match corresponding item tags further include instructions to perform matching between the items tags and the tags in the expanded profile data set. Each of the item tags can includes an item tag within a single most-specific level of each tag hierarchy describing each of the available actions, services, products and/or activities. The instructions to get item tags can also include instructions to expand each of the item tags to provide an expanded item tag data set that includes each higher-level tag to which each of the stored profile tags belongs in each tag hierarchy.

In another example, the instructions are further programmed to preprocess the item tag data set to select and/or disqualify a subset of the item tags based on particular conditions being satisfied for the given user.

In another example, the instructions to determine which of the tags in the expanded profile tag data set match corresponding item tags further can include instructions to apply journey tags for the given user.

In another example, the instructions can be programmed to generate a user interface to present intake questions and receive responses to the intake questions in response to user inputs, the profile tags for the given user being stored based on the responses to the intake questions.

The instructions further can include instructions to provide journey tags for the given user to encode where the given user is in a journey map, in which the journey map defines a sequence of stages predicting a progression to achieve a health-related and/or wellness goal for the given user, each stage of the journey map includes one or more tags defined by the hierarchical data schema, and journey tags are stored for the given user based on the responses to the intake questions. A journey map may be expertly defined or defined using machine learning algorithms.

As another example, a system includes one or more non-transitory machine-readable media to store instructions and data. The data can include a hierarchical tag database that includes a plurality of tags arranged according to a hierarchical data schema for a number of tag hierarchies, in which each tag hierarchy has one or more levels, each level in a respective tag hierarchy includes one or more tags, and tags within each level of a respective tag hierarchy have a different specificity relative each other level of the respective tag hierarchy. The data can also include profile tag data for a given user, in which the stored profile tag data for the given user includes one or more tags that have been assigned for the given user at a respective level in an associated tag hierarchy defined by the hierarchical data schema. The system can also include a processor configured to access the media and execute the instructions to perform a method. The method can include expanding each of the stored profile tags for the given user to provide an expanded profile tag data set for the given user, in which the expanded profile tag data set includes each of the assigned profile tags and each one or more higher-level tag in each associated tag hierarchy to which each of the assigned profile tags belongs. The method can also include determining which tags in the expanded profile tag data set match corresponding item tags representative of available actions, services, products and/or activities. The method can also include generating a results list representative of a matching set of the actions, services, products and/or activities based on the determination. The system can also include an output device configured to present at least a portion of the results list in a user-perceptible format.

DETAILED DESCRIPTION

Figure 1:
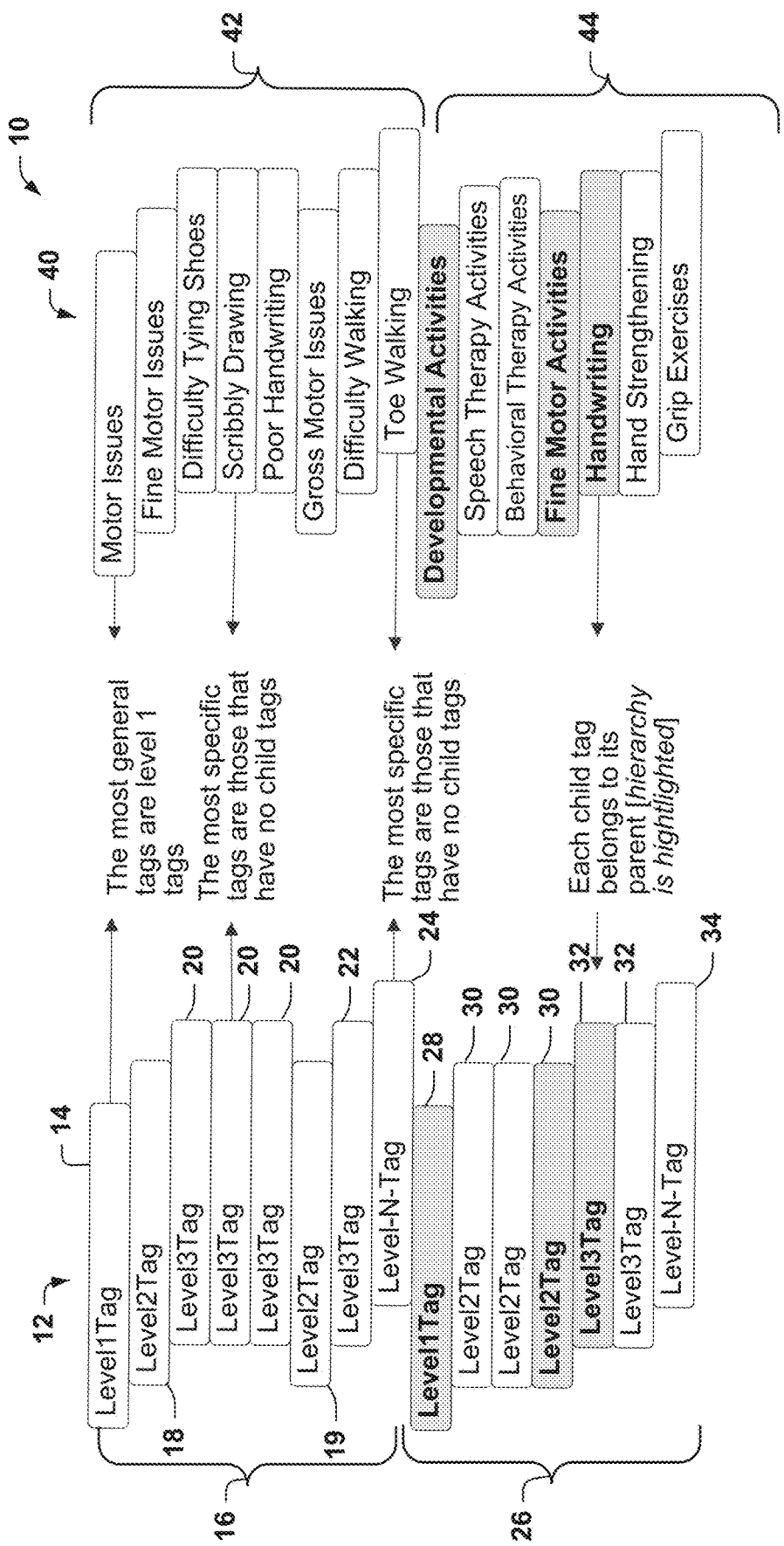
FIG. 1 depicts a generalized structure of an example tag hierarchy.

Examples of methods and systems for matching a user's situation to recommended items, which can include activities, actions, products, and services, are described herein. While many examples described herein relate to the user being a patient or caregiver, such as a parent or child, in the context of healthcare, the methods and systems described herein are equally applicable to perform matching to provide recommendations, also or as an alternative, to items in other contexts, such as relating to disease prevention, parenting, wellness and/or an individual's wellbeing. Thus, in many examples, the term "patient" herein can be replaced by "user" or "individual."

The methods and systems includes a hierarchical model for identifying the applicability of these activities, actions, products, and services, the means of dynamically matching a patient's situation to these activities, actions, products, and services using this model, and a means of iteratively updating the patient's recommendations and situation to ensure that the recommendations remain timely and current. The hierarchical model works by representing an activity, action, product, and/or service using a set of symbols henceforth called "tags," which are terms that represent the content, desired outcome, or concerning situation that the activity, action, product, or service is intended to address. These tags may be determined by processing textual descriptions of each available activity, action, product, or service, by entry by a domain expert in the field, or, in some examples, by a combination of both of these automatic and manual methods.

The collection of all available tags is built into a hierarchy within the model such that more-specific tags are categorized under related less-specific broader categories. Each tag is associated (e.g., mapped) to one or more categories. This arrangement of tags provides flexibility when evaluating the match between each item and patient as described below. This hierarchy is defined such that each tag has at most one generalization or, in some examples, multiple generalizing categories may be defined for the same tag. Allowing at most one generalization gives the benefit of simplified processing. This hierarchy may be multiple levels deep; thus, a very specific tag may refer to a more general category which may in turn point to an even broader category. In this way, multiple levels of specificity may be examined.

As a further example, the patient's situation is evaluated and described using the same tags that are used to describe the actions, products, and services. The tags in the model provide a keyword lexicon for mapping (or relating) between terms and various activities, actions, products, and/or services that can be recommended. For patients, tags can describe current situations, interests, needs, and/or goals for each patient. For example, each patient has a unique profile that is generated (e.g., by a profile initializer) through self-guided completion of questionnaires designed to assess the user's situation. These questionnaires are designed to assess the user's needs in general and then, in some examples, to examine the details of those situations. In some examples, a given patient's tags can be augmented (e.g., added to and/or changed) by providers or other experts (e.g., through instructions entered via a user interface) as they interact with the patient, such as including an interview conducted in person or through telecommunications for the purpose of assessing the patient's situation for future matching.

The method used to match patient circumstances to recommended items, which can include activities, actions, products, and services, works by computing a score between the patient profile data and the item tags. The method can then determine the highest scoring results based on the matching. The results may be displayed to the user ranked to show the items having the highest score first or may be sorted by some other property. The set of results may be restricted to only those with a sufficiently high score or may be limited to a given number of items such that all items displayed have higher scores than those not displayed. Additionally, the system may take action in an automated manner based on the highest score, or based on all items with a sufficiently high score (e.g., a score that exceeds one or more thresholds).

FIG. 1 depicts an example of generalized structure 10 of the tag hierarchy. The left side of FIG. 1, shown at 12, shows a hierarchical structure of a plurality of generic tags, in which the level 1 tag is the highest level of a respective hierarchy 16 (e.g., an orphan tag in the top level), with one or more subordinate level (e.g., child) tags indented under the level 1 tag. The example hierarchy 16 includes two level 2 tags 18 and 19, in which the level 2 tag 18 has three level 3 tags 20, and the level 2 tag 19 has one level 3 tag 22 and one level n tag 24 (where n denotes a number of additional level tags under the level 3 tag 22). Within the hierarchy 16, for example, the level 2 tags 18 and 19 are subordinate to (e.g., a child of) level 1 tag 14, and the level 1 tag is the parent of the level 2 tags 18, and level 3 tags 20 (which are peers within the hierarchy 16) are subordinate to level 1 tag 14 and the level 2 tag 18, and so forth. Other than the level 1 tag, each other level tag can have any number of one or more tags.

FIG. 1 also shows another hierarchy of tags 24 that includes a level 1 tag 26 and three level 2 tags 30, in which one of the level 2 tags 30 has two level 3 tags 32, and one of the level 3 tags has one level n tag 34 (where n denotes a number of additional level tags under the level 3 tag 32). In the hierarchy 26, the highlighted level 3 tag 32 belongs to its parent level 2 tag, both of which belong to the parent (hierarch) level 1 tag 28. As described herein, each subordinate level tag has an increased level of specificity compared to its immediate parent tag in the respective hierarchy. Thus, a leaf tag (e.g., a child tag having no child tags) is the most specific, and each level 1 tag is the most general in a respective hierarchy. There can be any number of respective hierarchies having any number and arrangement of child tags in the overall tag hierarchy 12.

As a further example, on the right side of FIG. 1, is an example hierarchy, shown at 40, in the context of a developmental disability. For sake of simplicity and ease of explanation, the hierarchy 40 has the same arrangement as the generic hierarchy 12. The simplified example hierarchy 40 includes two respective hierarchies 42 and 44 in which each indented level indicates a child or level of specificity in context. The level 1 tag 46 of the hierarchy 42 is "motor issues" and the level 1 tag 48 of the hierarchy 44 is "developmental activities." For example, in the hierarchy, a "handwriting" tag is a child of a "fine motor skills" tag, which is a child of a "developmental activities" tag—the level 1 tag in the hierarchy 44. The hierarchy 40 could include any other tags of different levels of specificity according to application requirements, such as having as many levels as needed to determine the specificity of the health related tag. The levels indicated a child/parent relationship, where each level indicates a child tag. As shown, with each child defined, the level of specificity becomes more specific.

Figure 2:
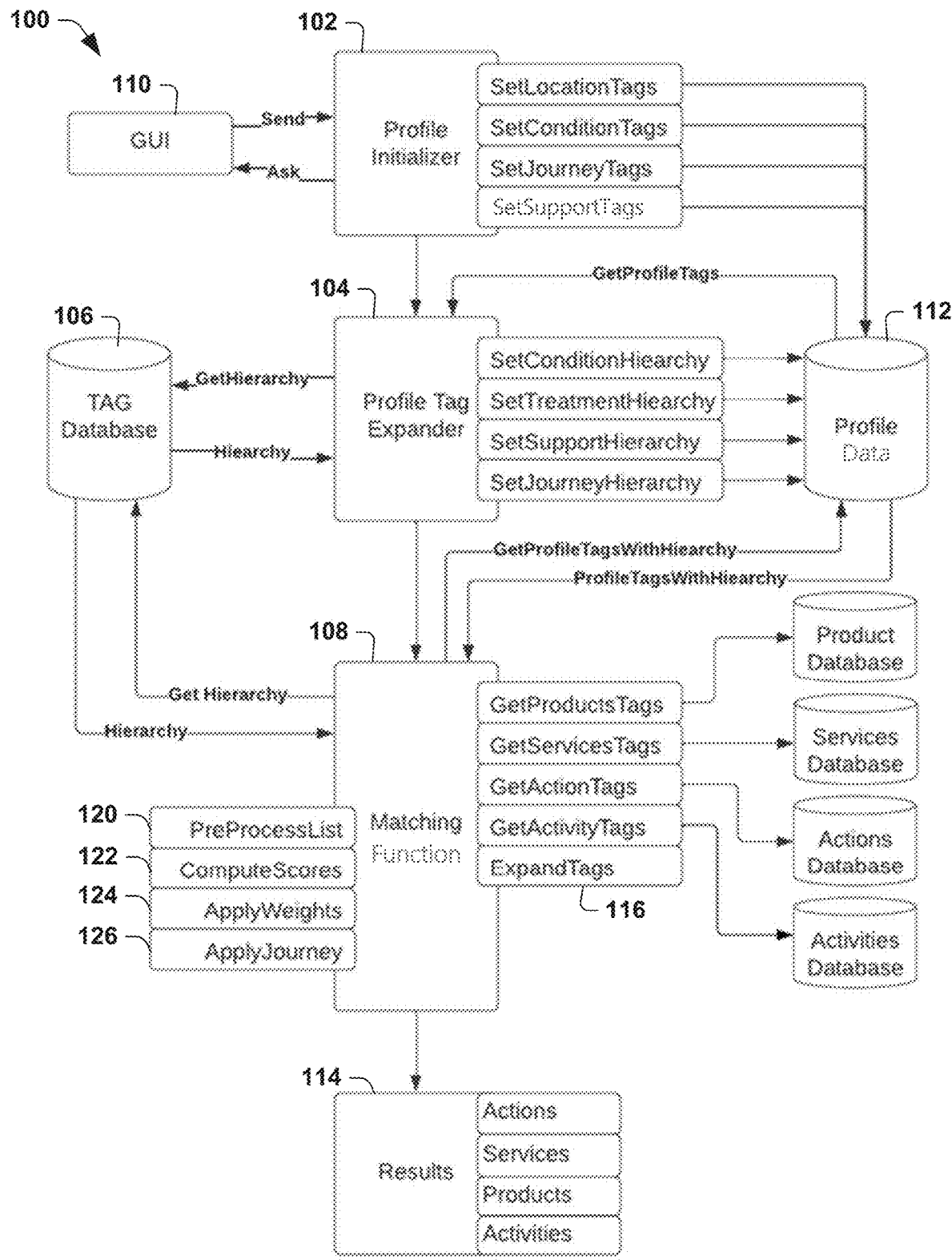
FIG. 2 depicts an example of system programmed to implement a process of collecting data and matching an individual to actions, products, and/or services.

FIG. 2 depicts an example of a system 100 programmed to perform a method of collecting data and matching an individual (e.g., patient) to actions, activities products, and/or services. The system 100 can be implemented on a computing system that includes one or more non-transitory computer readable media having data and instructions executable by one or more processors. The system 100 can be implemented at a premise, in distributed computing environment (e.g., a computing cloud) or a combination thereof. The system 100 includes a profile initializer 102, a profile tag expander 104, a tag database 106 and a matching function 108. The profile initializer 102 includes a graphical user interface (GUI) 110 to enable the system to generate profile data for a given user (e.g., patient).

For example, the profile initializer 102 is programmed to provide the GUI 110 to walk a user through a series of self-guided questions. The questions can be predetermined to evoke responses that can be selected from a set of predetermined response and/or include free text descriptive entries. The profile initializer 102 can include a response analyzer to automatically analyze response data to each question and determine one or more tags, such as defined in the tag database 106, which describe an attribute of the user related to each question. The analyzer can implement automatic matching, such as keyword matching, which can be used to analyze internally generated content or externally generated bodies of health content. The profile initializer 102 is programmed to map user responses (e.g., answers) to placement of tags into a respective user profile, which can be stored in a profile database 112. The profile initializer 102 can set a variety of tags based on responses to the questions, such from among hierarchical tags in tag database 106. For example, the profile initializer 102 can include instructions to set specific user tags stored in the profile database 112, including location tags, to set condition tags, to set journey tags and to set tags for available supports. In an example, the journey tags can encode the journey for each user (e.g., describing where each user is on their respective journey or journeys, as encoded by a respective journey map) using same hierarchical tagging structure described herein. Each patient profile can thus have the appropriate journey information encoded in its sets of tags, such as stored as journey tag data. The journey tag data can be maintained separately from profile data 112 or it can be part of the profile data.

In addition to the hierarchical tags, the profile initializer can encode additional information, such as relevance to the stage in a user/patient or health journey. There can be any number of journeys assigned to (or selected for) each user. For example, each life stage, health condition or progression towards a milestone (e.g., goal) is divided up into different stages or sets of stages that might branch (see, e.g., FIGS. 4 and 5). These stages indicate progress of diagnosis and treatment or progress towards a milestone (e.g., goal), rehabilitation, or improvement. These stages are determined on a per condition or per milestone, prescribed rehabilitation, or expected improvement basis and by domain experts. These stages may be augmented or defined, in part or in whole, by automated computational means. The stages are pre-defined by specific objective milestones that are achieved by the patient during their journey. Stages can be sequential and may be revisited to indicate reversions in the patient's journey based on analysis of the patient's tags. These stages define the expected change in a patient's tags over time and, in some examples, include specific activities, actions, products, and/or services relevant at each stage of the sequence, as defined by the journey map for the user. The journey tags can be representative of a user's journey information, which is collected by the GUI 110 through a set of the self-guided questions.

Also, or as an alternative, to reduce storage requirements and facilitate updating the tag database 106 independently of user profiles, the tags stored in the profile database 112 for each respective user can be limited to the most specific level within each hierarchy without also including each higher level tag to which the each tag belongs. Referring back to FIG. 1, for the example of the motor issue hierarchy 42, an individual having an issue with toe walking, only "the toe walking" tag would be stored in the profile database 112 as part of the user profile data, and associated parent tags "difficulty walking", "gross motor issues" and "motor issues" would not be stored as part of the user profile data. In other examples, one or more different level tags (e.g., higher or lower level tags) can be stored for a given user based on user responses and/or other information entered by or on behalf of the user because different user information, including responses, can map to different level tags within a respective tag hierarchy.

After the user profile has been generated for a given user, such as responsive to completing the series of intake questions, the system 100 is programmed to perform matching and generate results 114 for the user, which can include a results list of one or more recommended actions, services, products and/or activities. The system 100 can include instructions to display the results list or a selected portion thereof on an output device a (e.g., a display of a computing device, such as a computer, workstation, tablet computer, smart phone etc.) configured to present at least a portion of the results list in a user-perceptible format. The output devices can also provide the GUI 110 to enable user interaction with the system 100.

In an example, the system 100 can include respective databases for available actions, services, products and activities. Each such product, service, action and activity can be assigned one or more hierarchical tags, as defined the tag database 106. Such tags can be assigned in response to a user input, automatically or include some manual and some automated tagging of actions, services, products and activities. Similar to the profile tags in the profile data 112 for each user, the hierarchical tags stored in respective database for each action, activity, product, and service can include only the most specific tag that accurately describes the respective action, activity, product, or service.

The profile tag expander 104 is programmed to expand the profile for a respective user to include all 'parents' of the tags that are specified in the profile data 112. For example, a respective profile tag having a particular lower level is stored in the profile data 112, and the profile expander 104 uses the respective profile tag as an index to identify each parent tag to which the respective profile tag belongs up to the highest level tag (e.g., level 1 tag) in each respective hierarchy. The expansion does not include siblings or peers at the same level, but instead only includes direct parents up to the highest level parent in the respective hierarchy. In some examples, a given tag may exist in more than one hierarchy and at the same or a different level within each such hierarchy. In such example, the profile tag expander 104 is programmed to retrieve the expanded hierarchy tags from each such hierarchy where the given tag has been categorized. Thus, there duplicate tags likewise do not need to be stored in a given user's profile, further conserving system resources. The profile tag expander 104 thus can return the expanded hierarchies for each tag that is stored as part of the user's profile in 112.

In an example, the matching function 108 is programmed to request the profile tags with the respective expanded hierarchy (e.g., through a GetProfileTagsWithHierarchy request), which receives the response that includes the respective tags with the corresponding hierarchy (e.g., in a ProfileTagsWithHierarchy response). Additionally, the matching function 108 can include expand tags code 116 that is programmed to read (e.g., GetProductsTags, GetServicesTags, GetActivityTags, GetActionTags code) and to expand (e.g., ExpandTags code 116, such as by invoking an instance of the profile tag expander 104) each action, activity, product, and service database in the same or similar same manner. Each action, activity, product, and service database can be stored in a cloud-based storage system and/or in local memory. The collective set of tags in each action, activity, product, and service database can be referred to as item tag data, and the expanded versions thereof can be referred to as expanded item tag data. The item tag data can be programmatically link to or otherwise specify a set of respective actions, services, products and activities.

The matching function 108 includes code is programmed to perform analysis and calculations based on the expanded profile tag data and the expanded item tag data to determine the results set 114 containing a set of matching actions, activities services, and/or products. In the example of FIG. 2 the matching function code 108 includes a PreProcessList code 120, ComputeScores code 122, ApplyWeights code 124 and ApplyJourney code 126. For example, the PreProcessList code 120 is programmed to select a subset of the item tags or disqualify (e.g., filter out) another subset of the item tags based on certain conditions being met for the given user. The PreProcessList 120 code can employ one or more criteria to determine the subset of item tags for each of the respective item database. Examples of such criteria include the user's age range tag, the user's journey tag data. For instance, the journey tag data specifies a respective journey and stage of the respective journey (as well as other journey-specific and/or stage-specific information) for the given user. The PreProcessList code 120 can invoke the ApplyJourney code 126 can further constrain to item tags based on the respective user's journey tag data. The PreProcessList code 120 can also be programmed to remove item tags already consumed, such as based on the matching function already selecting a given one or more item tags. The PreProcessList code 120 thus operates to reduce the size of the matching task by including relevant tag data and/or excluding certain other tag data, such that the matching function code can operate faster and more efficiently.

The ApplyWeights code 124 can be programmed to increase relative weighting of more specific tags within each respective tag hierarchy, such as according to a weighting schedule. In one example, the weighting schedule is configured to reduce the weight (e.g., by ½) for items residing each level up the hierarchy from the most specific tag. Other types of weighting can be used in other examples. In some examples, the matching function 108 is programmed to perform matching with respect to children only and apply the ApplyWeights code 124 and compute scores for all tags in the expanded data sets. The ComputeScore code (see, e.g., FIG. 3) can compute a match based on the matching, which can be a weighted match from applying the ApplyWeights code 124. The results 114 can include a ranked list of the best matching activities, actions, services, and/or products.

The matching function can be programmed to implement keyword matching based on current state of the profile data 112, based on a historical version of the profile data 112 and/or based on predictive version and/or trends in the profile data. The historical version of the profile tag data 112 can include a set of profile tags at one or more prior stages of the journey and/or the profile tags within each stage of the journey throughout the journey. In another example, the system 100, including the matching function 108, is programmed to implement machine learning or an expert system, such as to modify results provided by the matching function automatically and/or in response to a user input instruction from a domain expert. The user input instructions can be provided to approve one or more actions, services, products or activities provided in the results 114. Also, or as an alternative, the user input instructions can be provided to adjust one or more actions, services, products or activities provided in the results 114, which can be provided by the matching function. This along with other functions described herein enables the system to provide a personalized plan of activities, actions, services, and/or products for each particular user.

Additionally, the user profile for each user further can be updated periodically (e.g., daily, weekly or at other time intervals) and/or in response to a detecting a trigger condition (e.g., automated trigger or in response to a manual user input instruction). The updating of the user profile can involve adding and/or changing one or more tags in the profile data 112 and/or journey tag data for the given user. The system 10 can be programmed to invoke the matching function 108 to responsive to such changes and/or additions to the user and generate a new set of recommendations for a given user based on the current profile in the profile data 112 and the current set of available items, including products, services, actions and activities.

Figure 3:
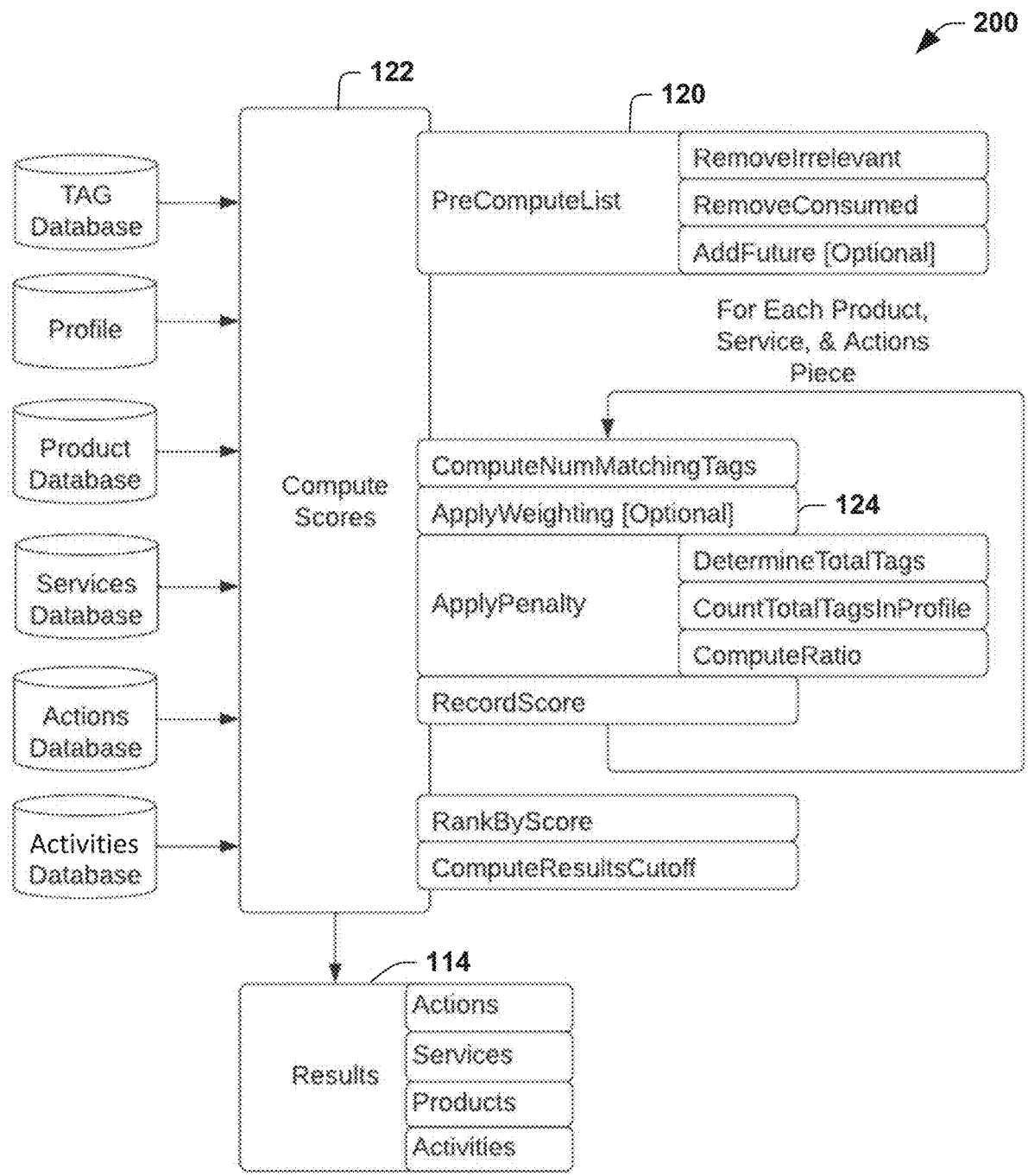
FIG. 3 depicts an example of a score calculation system.

FIG. 3 depicts an example of a score calculation system 200. The score calculation system 200 is a useful example of the ComputeScores code 122 described with respect to the matching function 108 of FIG. 2. Accordingly, the description of FIG. 3 can refer back to the description of FIG. 2. As mentioned, the compute score code, which is programmed to compute the scores for each action, activity product, and service, can start with a pre-computation (e.g., PreProcessList code 120) programmed to remove from the list of computations to be performed a set of the irrelevant and already consumed products and services, and previously completed actions. Potential predictive future actions, products, and services that contain tags that might be added based on the patient journey phase can be added to the list to be computed.

The score calculation system 200 is programmed to compute scores on remaining items by first computing the number of matching tags between the profile data (e.g., defined in the expanded profile tag data) and each individual action, activity, service, and product (e.g., as defined in the expanded item tag data). This score can be computed with equal weights or can be weighted to increase or decrease the contribution of certain tags based on experts. A penalty for those actions, activities, products, and services can then be applied by adjusting the respective scores based on computing a ratio of the number of tags matched to the total tags in the definition of each action, activity, product, or service.

Finally, the score calculation system 200 is programmed (e.g., by executing RankByScore code) to rank the list of scores and determine the number of results to be returned, such as based on pre-defined cutoff criteria is determined. The resulting list of recommended actions, services, and products is then presented as results data to the user (e.g., patient) on a display device through the graphical user interface (GUI) in a manner that can be sequentially executed or consumed by the patient.

As a variation to this process, an automated system may determine applicable actions as described above, and take action based on the top results, and/or the results above a threshold which is predetermined or determined by analysis of the distribution of the scores.

As a further example, with reference to FIG. 3, the score calculation system 200 can be programmed to execute the following method:

1. First, specific patient data is obtained, such as through a self-guided questionnaire.
2. The specific-patient data, including location, condition, and available supports, is stored in a database. Journey information is collected as well through a series of self-guided questions.
3. The set of tags that are set by the questionnaire are then expanded (e.g., by profile tag expander code) to include all the generalized tags stored in the tag database.
4. This expansion process can be recursive, where each tag is examined for a parent, and if a parent exists, the parent tag is added to the patient profile (e.g., profile 112).
5. This set is then processed to remove duplicates resulting from the tag expansion.
6. Similar to steps 1-5, the tags for the actions, activities products, and services are expanded. The tags can be stored in respective databases (or in a single database) for each of the available actions, activities products, and services.
7. Then, the expanded tags in the patient profile are compared to the expanded tags in the set of actions, products, and services.
8. The list of potential actions, products, and services may be pre-processed to reduce the number of scores that need to be computed. This pre-processed list may exclude completed actions or previously consumed products and services as well as those that are determined to be irrelevant.
9. For each tag that is exactly the same between the profile and each potential action, product, or service, the score is increased.
10. This process is repeated for each action, product, or service is being scored.
11. The total number of tags defined in each action, product, and service is computed.
12. The match score is then computed as the ratio of number of matching tags to the number of total tags for each action, product, or service.
13. These scores are effectively the percentage of tags defined or implied by the item which are also defined or implied by the patient. In this way, the match score will be higher for items that address the user's circumstances without addressing additional items. The score is, therefore, higher for items that are more specifically applicable to the patient and penalizes those actions, products, and services that are effectively broader.
14. In some examples, weighting can be used when expanding parent tags for each set in steps 3-5. Additional weights can be increased for those tags that are determined to be more important, such as specified by domain experts. As an example, all tags can have a weight of 1 because the count of the tags is used. In an example when weighting is applied (e.g., by Apply-Weighting code), a value of 1 can be assigned to all tags in the original set before tag expansion, and then assign a new (e.g., different or lesser) value for tags added through the resolution process.

15. The original set of tags may be augmented, such as by adding the descendants of a broader group and assigning a value to these based on a predefined patient journey. In this way, the matching score can be configured to consider items that do not directly address the patient's current circumstances but which may be helpful otherwise.
16. Should items directly addressing the patient's circumstances be available, they will have a higher score. Should they not be available, these related items will have a sufficiently high score to be shown.
17. The patient's tags can then be augmented with the tags that are expected for the user in the future. When these tags are added, they may be assigned a score. The set of tags is then re-expanded to account for the new tags. In this way, the user's future needs can be considered even before the user is aware that they have them. Items associated with this transition may also have their score modified by setting their score to a known constant value or by modifying the score computed for the user through some other equation.

Figure 4:
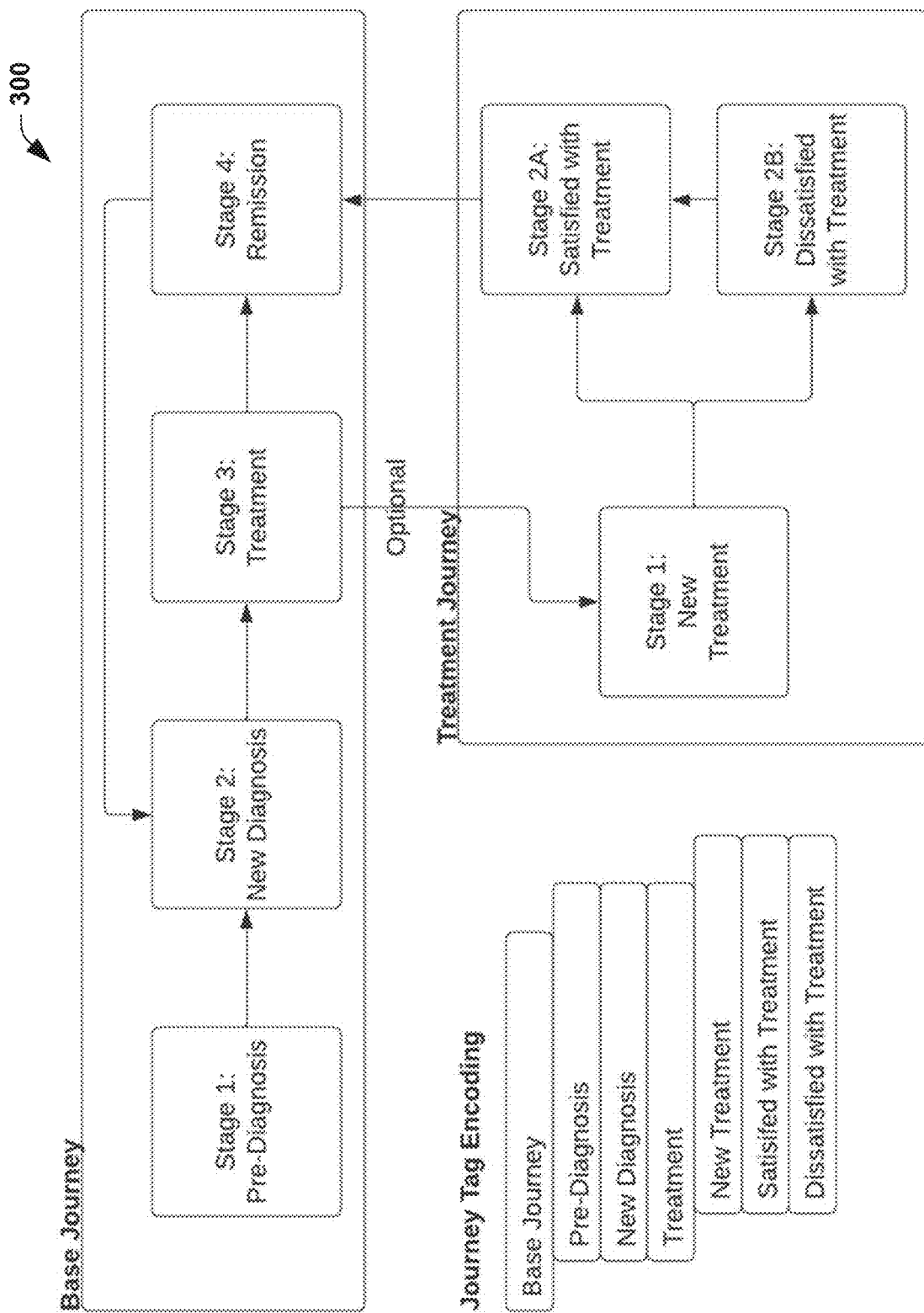
FIG. 4 is a block diagram showing an example of a journey.

FIG. 4 is a block diagram showing an example of a journey map 300, which defines a sequence of stages related to a disease condition. As an example, in FIG. 4, an example journey definition can be as follows: Each patient may have a condition or a set of conditions that is associated with a specific patient journey. The journey map can be described using a flowchart and can be expertly determined. The journey can be further subdivided into other journeys. After these journey maps are defined, they can be encoded using the same hierarchical tagging structure described herein (see, e.g., FIG. 1). Each patient profile can then have the appropriate journey information encoded in its sets of tags to provide journey tag data, which can be part of or in addition to the profile, as well as each action, activity, product, and service. The journey tags can be used (e.g., by the system 100) to predict the next set of activities, actions, services, and/or products suited to the user's journey and, particularly, where the user is in the journey map (as described by the journey tags). The example journey map 300 of FIG. 4 can be used to provide recommendations for a patient condition, such as a disease or illness. The journey map 300 includes four stages: pre-diagnosis, new diagnosis, treatment and remission. Also, the treatment stage includes a respective treatment journey having a set of associated stages.

Figure 5:
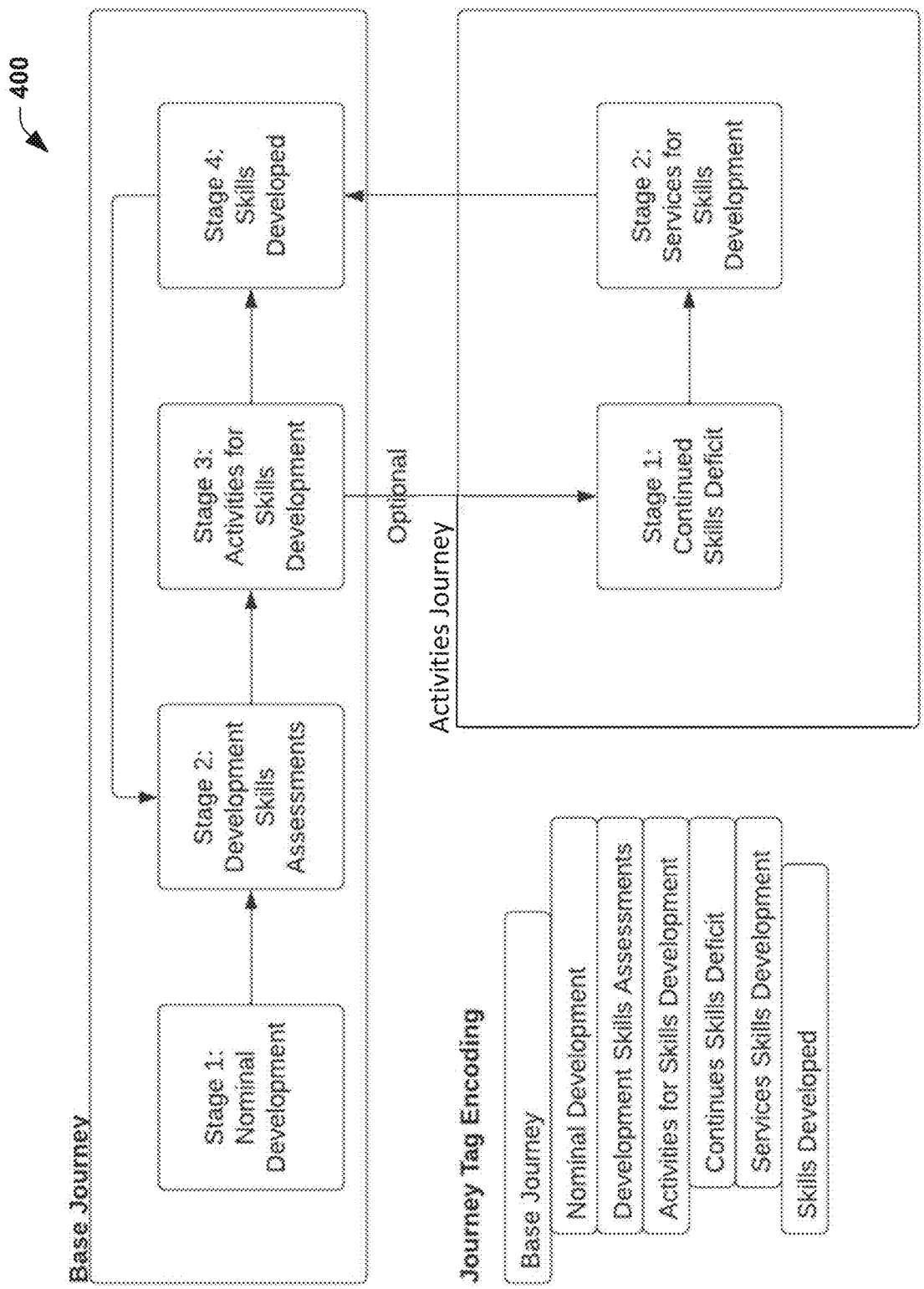
FIG. 5 is a block diagram showing of another example of a journey.

FIG. 5 is a block diagram showing of another example of a journey map 400, such as for developing one or more skills. The journey map includes a base journey having four stages: nominal development, development skills assessment, activities for skills development and skills developed. The activities stage (stage 3) can also include an activities journey having a set of associated stages. A journey for a parent, for example, is how they traverse the journey map 400 with and/or on behalf of their child, such as can involve actions, activities, services and products. As shown in the journey map 400, there are optional paths and potential setbacks that a parent/patient may have in their journey.

Journey maps can be provided for various other conditions, problems or issues, such as pertaining to health, healthcare, well-being, behavior, wellness or other user conditions relating to various individuals, such as including patients, parents and their children.

As a further example, to ensure that the actions, products, and services recommended to the user remain relevant and timely, the user's situation can be modified through some or all of the following:

1. New questionnaires may be given as recommended actions or using a schedule. These questionnaires are designed to assess the changes in the patient's circumstances and adjust their tags accordingly.
2. As the patient interacts with the providers of products and services, those providers may update the patient's set of tags.
3. As the user completes actions or activities, or consumes products and services, their profile data 114 can be updated. For example, the updates to the profile data is based on definitions provided by experts when those items were created and/or by tracking the tags for items that a user consistently consumes but are not currently part of their set of the user's profile tags.
4. This process may also take into consideration the sequences of tag changes when determining the likelihood that a tag is applicable to a user based on their consumption of items (e.g., performing actions or services or activities and/or using products), including those recommended in the results 114.
5. The set of recommendations can be recomputed based on this updated profile, either on request from the user, or periodically.
6. Additionally, the change in recommendations can be determined by the system 100 and displayed to the patient.

Figure 6:
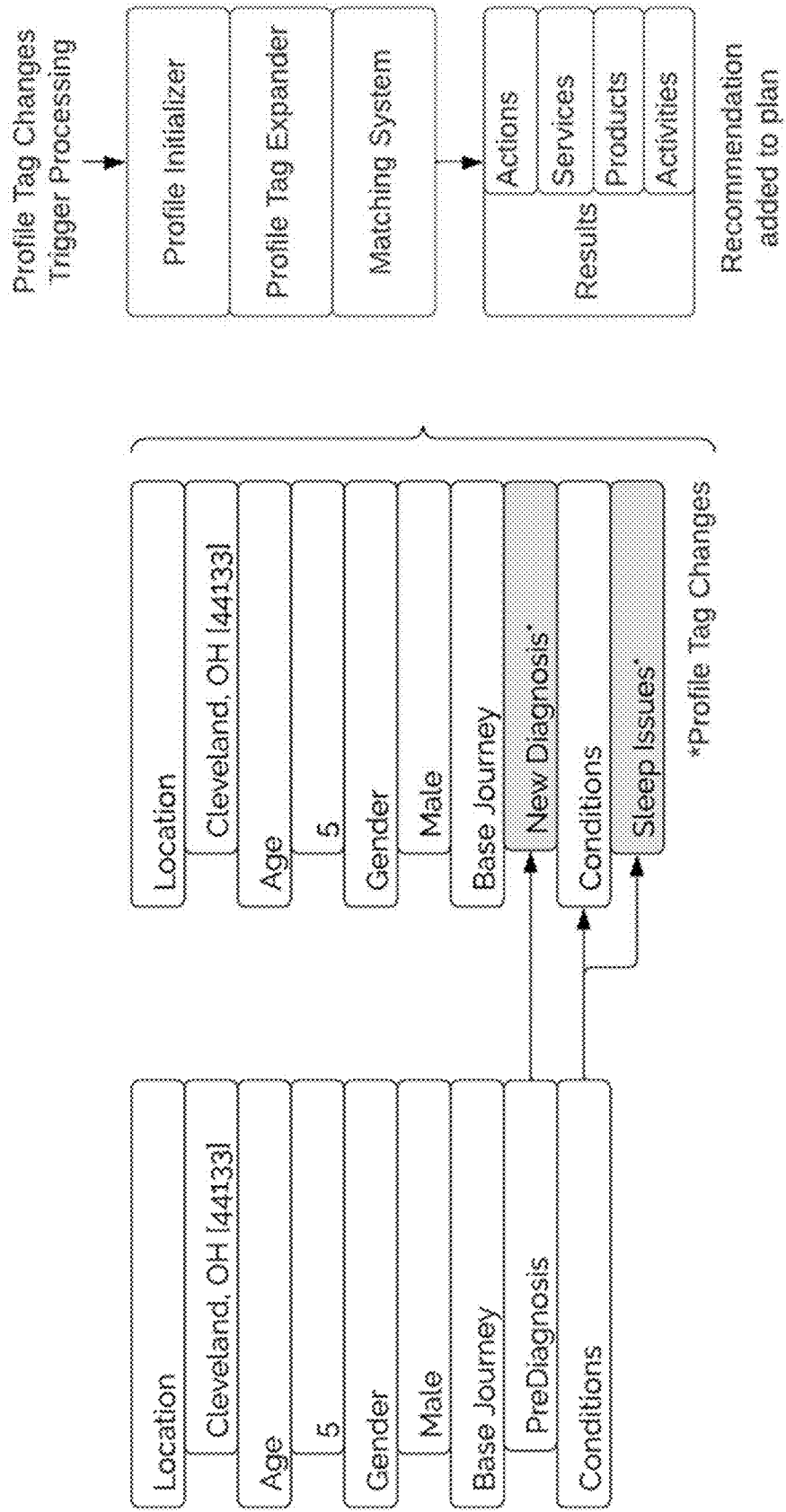
FIG. 6 is a block diagram showing a profile update triggering new recommendations.

FIG. 6 is a block diagram showing a profile update triggering new recommendations.

FIGS. 7-11 are example GUIs that can be implemented as part of the systems and methods described herein.

Figure 7:
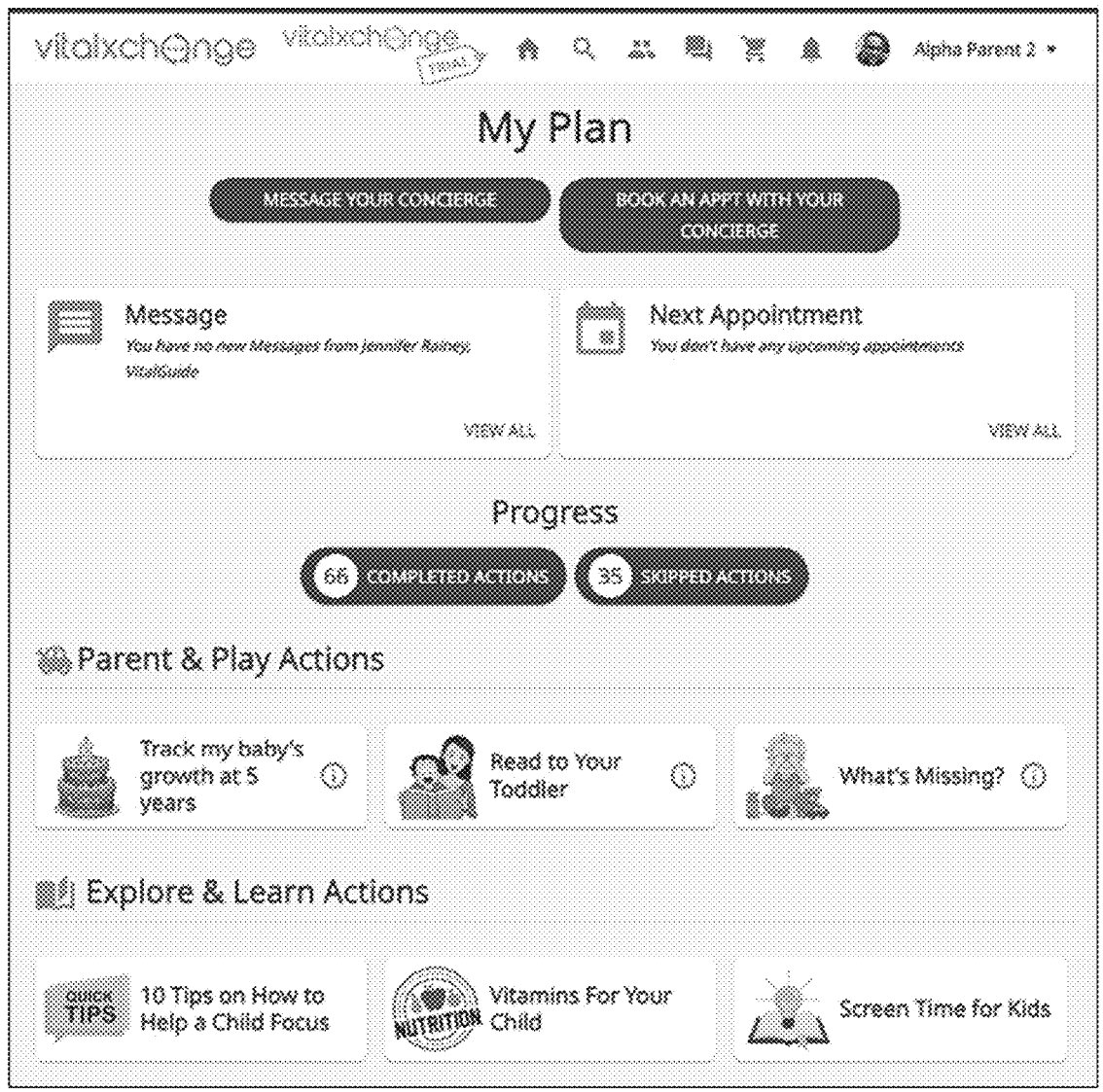
FIG. 7 is an example GUI showing activities, actions, and products in a plan.

FIG. 7 is an example GUI showing activities, actions, and products in a plan.

Figure 8:
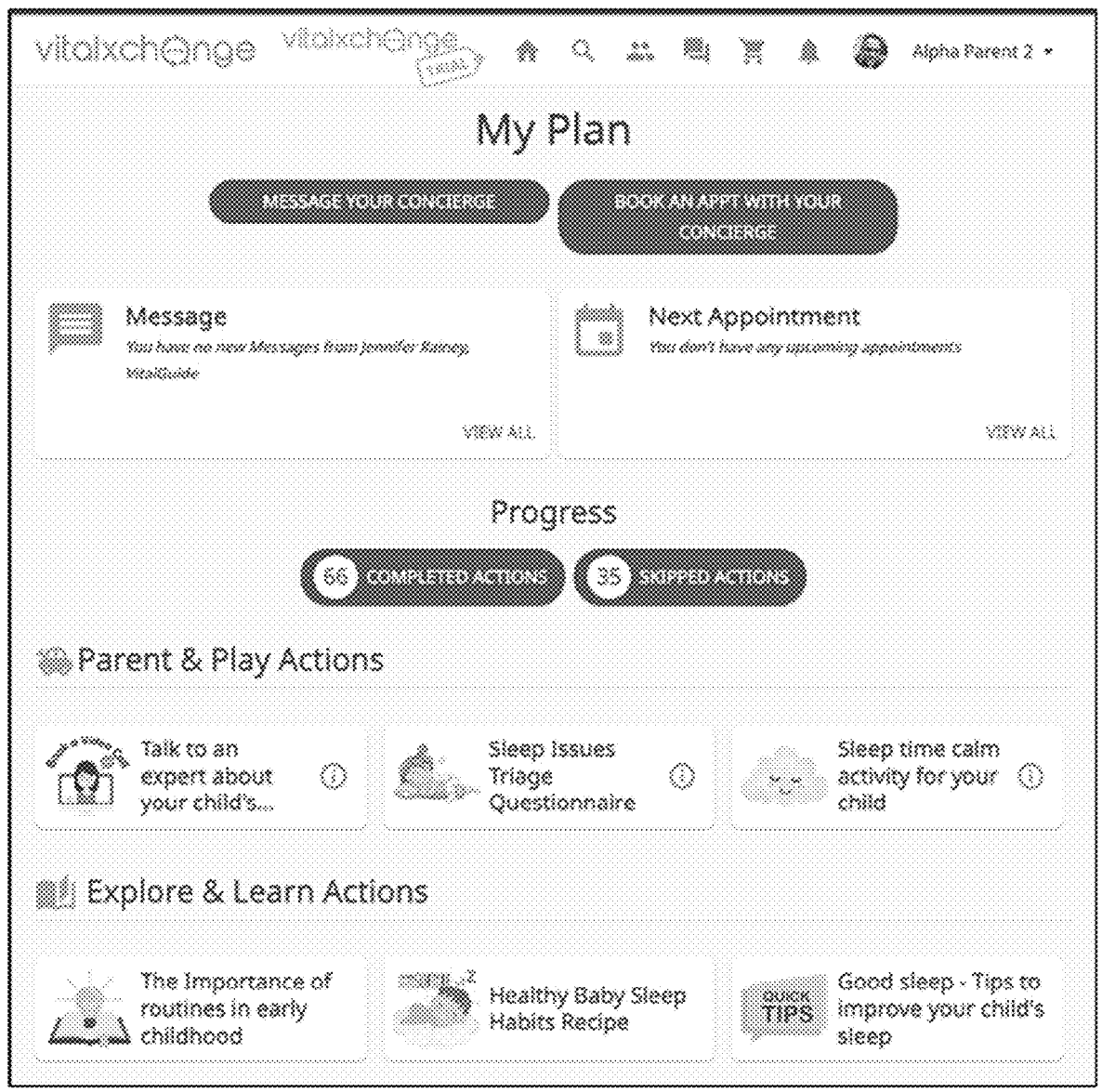
FIG. 8 is an example GUI showing an updated plan of activities, actions, and services from a profile update.

FIG. 8 is an example GUI showing an updated plan of activities, actions, and services from a profile update.

Figure 9:
FIG. 9 is an example GUI for a plan review interface that can be used by an authorized user for reviewing plan recommendations.

FIG. 9 is an example GUI for a plan review interface that can be used by an authorized user for reviewing plan recommendations.

Figure 10:
FIG. 10 is an example GUI for a plan review interface that can be used by an authorized user for reviewing recommendations to add to a plan.

FIG. 10 is an example GUI for a plan review interface that can be used by an authorized user for reviewing recommendations to add to a plan.

Figure 11:
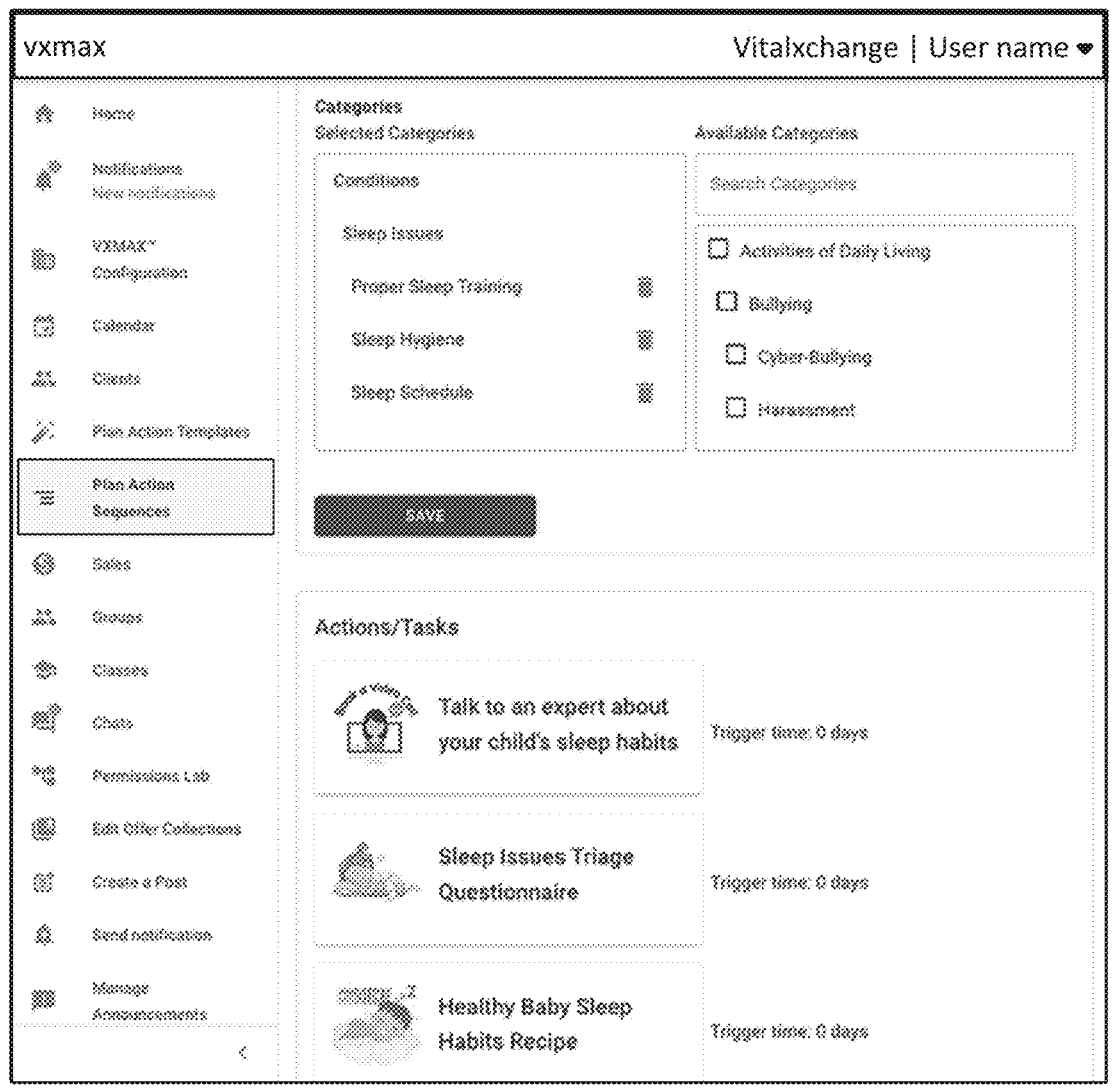
FIG. 11 an example GUI for reviewing time-triggered recommendations.

FIG. 11 an example GUI for reviewing time-triggered recommendations.

As will be appreciated by those skilled in the art, portions of the systems and methods disclosed herein may be embodied as a method, data processing system, or computer program product (e.g., a non-transitory computer readable medium having instructions executable by a processor). Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments are disclosed herein with reference to flowchart illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in a non-transitory computer-readable medium that can direct a computer or other programmable data processing apparatus (e.g., one or more processing core) to function in a particular manner, such that the instructions stored in the computer-readable medium result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks or the associated description.

What are disclosed herein are examples. It is, of course, not possible to describe every conceivable combination of components or methods, but one of ordinary skill in the art will recognize that many further combinations and permutations are possible. Accordingly, the disclosure is intended to embrace all such alterations, modifications, and variations that fall within the scope of this application, including the appended claims.

What is claimed is:

1. One or more non-transitory computer readable media having instructions, which when executed by one or more processors are programmed to at least:
    store a hierarchical tag database that includes a plurality of tags arranged according to a hierarchical data schema for a number of tag hierarchies, in which each tag hierarchy has one or more levels, each level in a respective tag hierarchy includes one or more tags representative of related concepts associated with the respective tag hierarchy, and tags within each level of a respective tag hierarchy have a different specificity relative to each other level of the respective tag hierarchy, in which a tag at a given level of a given tag hierarchy represents a more specific concept than the respective tag in each level that is higher than the given level in the respective tag hierarchy;
    store profile tags for a given user, in which the stored profile tags for the given user include one or more tags of the plurality of tags that have been assigned to the given user at a respective level in an associated tag hierarchy defined by the hierarchical data schema;
    perform matching between the profile tags and item tags representative of actions, services, products and/or activities, wherein the item tags include respective tags in the associated tag hierarchy defined by the hierarchical data schema, and wherein the instructions to match further include instructions to:
        expand each of the stored profile tags for the given user based on the associated tag hierarchies in the hierarchical tag database that include the stored profile tags to provide an expanded profile tag data set for the given user, in which the expanded profile tag data set includes each of the assigned profile tags and each one or more higher-level tags in each associated tag hierarchy that are at a higher level than the assigned profile tag in the associated tag hierarchy to which each of the assigned profile tags belongs;
        determine which tags in the expanded profile tag data set match corresponding item tags representative of available actions, services, products and/or activities, and
    generate a results list representative of a matching set of the actions, services, products and/or activities for the given user based on the determination.

2. The media of claim 1, wherein the instructions further include instructions to compute a score for each of the matches determined between the item tags and the tags in the expanded profile tag data set, in which the score for each of the matches depends on the level of hierarchy for each of matching tags, and the set of the actions, services, products and/or activities arranged in the results list is based on the respective scores.

3. The media of claim 2, wherein the instructions to compute the score is programmed to compute the score based on at least two of:
    a number of matching tags;
    a weighting applied to each of the matching tags according to weighting schedule;
    a penalty applied to reduce a value of the respective scores based on an absolute and/or relative quantity of matching tags.

4. The media of claim 1, wherein each of the stored profile tags for the given user includes a tag within a single most-specific level of each associated tag hierarchy that has been assigned for the given user,
    wherein the hierarchical tag database is changed independently of the stored profile tags for the given user, and
    wherein the assigned profile tags for the given user are expanded based on the associated tag hierarchies in the updated hierarchical tag database, whereby changes to the hierarchical tag database are reflected in the expanded profile tag data set for the given user.

5. The media of claim 4, wherein the instructions to expand the assigned profile tags for the given user are further programmed to:
    search the tag database containing a complete hierarchical description for tags within each tag hierarchy defined by the hierarchical data schema;
    identify each higher-level tag to which each of the stored profile tags belongs in each of the tag hierarchies; and
    generate the expanded profile tag data set for the given user to include each of the stored profile tags and each of the identified higher-level tags in each of the tag hierarchies.

6. The media of claim 1, wherein the instructions are further programmed to get item tags assigned to each of the available actions, services, products and/or activities, and the instructions to determine which of the tags in the expanded profile tag data set match corresponding item tags further include instructions to perform matching between the items tags and the tags in the expanded profile data set.

7. The media of claim 6, wherein:
    each of the item tags includes an item tag within a single most-specific level of each tag hierarchy describing each of the available actions, services, products and/or activities, and
    the instructions to get item tags includes instructions to expand each of the item tags to provide an expanded item tag data set that includes each higher-level tag to which each of the stored profile tags belongs in each tag hierarchy.

8. The media of claim 7, wherein the instructions are further programmed to preprocess the item tag data set to select and/or disqualify a subset of the item tags based on particular conditions being satisfied for the given user.

9. The media of claim 1, wherein the instructions further include instructions to provide user-specific journey tags for the given user to encode where the given user is in a journey map, in which the journey map defines a sequence of stages describing a progression of objective milestones to achieve a health-related and/or wellness goal for the given user, each stage of the journey map includes one or more journey tags defined by the hierarchical data schema, wherein the instructions to determine which of the tags in the expanded profile tag data set match corresponding item tags further include instructions to apply the user-specific journey tags for the given user and constrain the item tags for the given user based on the applied user-specific journey tags to include one or more actions, services, products and/or activities relevant to where the given user is in the journey map.

10. The media of claim 1, further including instructions to generate a user interface to present intake questions and receive responses to the intake questions in response to user inputs, the profile tags for the given user being stored based on the responses to the intake questions.

11. The media of claim 10, wherein the instructions further include instructions to provide user-specific journey tags for the given user to encode where the given user is in a journey map, in which the journey map defines a sequence of stages describing a progression of objective milestones to achieve a health-related and/or wellness goal for the given user, each stage of the journey map includes one or more journey tags defined by the hierarchical data schema, and user-specific journey tags are stored for the given user based on the responses to the intake questions.

12. The media of claim 11, further comprising instructions to augment the assigned profile tags for the given user to include one or more new tags that are expected for the given user at a future time in the journey map, and the augmented assigned profile tags for the given user, including the one or more new tags, are expanded to provide an augmented expanded profile tag data set for the given user such that the matching is based on the augmented expanded profile tag data set for the given user.

13. A system comprising:
one or more non-transitory machine-readable media to store instructions and data, wherein the data includes:
a hierarchical tag database that includes a plurality of tags arranged according to a hierarchical data schema for a number of tag hierarchies, in which each tag hierarchy has one or more levels, each level in a respective tag hierarchy includes one or more tags, and tags within each level of a respective tag hierarchy have a different specificity relative each other level of the respective tag hierarchy; and
profile tag data for a given user, in which the stored profile tag data for the given user includes one or more tags that have been assigned for the given user at a respective level in an associated tag hierarchy defined by the hierarchical data schema;
a processor configured to access the media and execute the instructions to perform a method comprising:
expanding each of the stored profile tags for the given user to provide an expanded profile tag data set for the given user, in which the expanded profile tag data set includes each of the assigned profile tags and each one or more higher-level tag in each associated tag hierarchy to which each of the assigned profile tags belongs;
determining which tags in the expanded profile tag data set match corresponding item tags, wherein the item tags include respective tags in the associated tag hierarchy defined by the hierarchical data schema and the item tags are representative of available actions, services, products and/or activities;
generating a results list representative of a matching set of the actions, services, products and/or activities based on the determination; and
an output device configured to present at least a portion of the results list in a user-perceptible format.

14. The system of claim 13, wherein the expanding is invoked in response to or as part of executing the instructions to perform the matching.

15. The system of claim 13, wherein the method performed by the instructions further include:
computing a score for each of the matches determined between the item tags and the tags in the expanded profile tag data set, in which the score for each of the matches depends on the level of hierarchy for each of matching tags, and the set of the actions, services, products and/or activities arranged in the results list is based on the respective scores.

16. The system of claim 13, wherein each of the stored profile tags for the given user includes a tag within a single most-specific level of each associated tag hierarchy that has been assigned for the given user, and the expanding further includes:
searching a tag database containing a complete hierarchical description for tags within each tag hierarchy defined by the hierarchical data schema;
identifying each higher-level tag to which each of the stored profile tags belongs in each tag hierarchy; and
generating the expanded profile tag data set for the given user to include each of the stored profile tags and the identified higher-level tags in each of the tag hierarchies.

17. The system of claim 13, wherein the method performed by the instructions further includes getting item tags assigned to each of the available actions, services, products and/or activities, and the determining further includes matching between the items tags and the tags in the expanded profile data set.

18. The system of claim 17, wherein:
each of the item tags includes an item tag within a single most-specific level of each tag hierarchy describing each of the available actions, services, products and/or activities, and
getting further includes expanding each of the item tags to provide an expanded item tag data set that includes each higher-level tag to which each of the stored profile tags belongs in each tag hierarchy.

19. The system of claim 13, wherein the instructions to perform the method further includes at least one of:
preprocessing the item tag data set to select and/or disqualify a subset of the item tags based on particular conditions being satisfied for the given user; or
applying journey tags for the given user to determine which of the tags in the expanded profile tag data set match corresponding item tags.

20. The system of claim 13, wherein the method performed by the instructions further includes:

providing a user interface to present intake questions and receive responses to the intake questions in response to user inputs;

storing the profile tags for the given user based on the responses to the intake questions; and storing journey tags for the given user to encode where the given user is in a journey map, in which the journey map defines a sequence of stages describing a progression to achieve a goal for the given user, each stage of the journey map includes one or more tags defined by the hierarchical data schema, and journey tags are stored for the given user based on the responses to the intake questions.

* * * * *